(12) United States Patent
Svoboda (10) Patent No.: US 11,801,107 B1
(45) Date of Patent: Oct. 31, 2023

(54) STERILIZED GLOVE DISPENSER ASSEMBLY

(71) Applicant: Sharla Svoboda, Wharton, TX (US)

(72) Inventor: Sharla Svoboda, Wharton, TX (US)

( * ) Notice: Subject to any disclaimer, the term of this patent is extended or adjusted under 35 U.S.C. 154(b) by 0 days.

(21) Appl. No.: 17/879,881

(22) Filed: Aug. 3, 2022

(51) Int. Cl.
*A61B 42/50* (2016.01)
*A61B 42/40* (2016.01)

(52) U.S. Cl.
CPC .............. *A61B 42/50* (2016.02); *A61B 42/40* (2016.02)

(58) Field of Classification Search
CPC .......... A61B 42/50; A61B 42/40; A47G 25/80
USPC .......................................................... 221/69
See application file for complete search history.

(56) References Cited

U.S. PATENT DOCUMENTS

| | | | | |
|---|---|---|---|---|
| 1,938,685 | A * | 12/1933 | Breuls | A61B 42/40 223/111 |
| 4,915,272 | A | 4/1990 | Vlock | |
| 5,868,290 | A * | 2/1999 | Green, Sr | A47G 25/904 223/111 |
| 6,053,380 | A * | 4/2000 | Sherrod | A47G 25/904 223/111 |
| D440,740 | S | 4/2001 | Anctil | |
| 10,912,405 | B1 | 2/2021 | McCarthy | |
| 11,324,562 | B2 * | 5/2022 | Moghadam | A61B 42/50 |
| 2006/0010563 | A1 * | 1/2006 | Michel | A61B 42/50 2/159 |
| 2010/0147909 | A1 * | 6/2010 | Kelly | A61B 42/50 223/111 |
| 2011/0186589 | A1 | 8/2011 | Lee | |
| 2017/0014198 | A1 * | 1/2017 | Gravlee | A47G 25/90 |
| 2019/0159619 | A1 * | 5/2019 | Burk | A47G 25/904 |
| 2023/0032175 | A1 * | 2/2023 | Brett | A47G 25/904 |
| 2023/0033618 | A1 * | 2/2023 | Waineo | B65G 1/06 |

FOREIGN PATENT DOCUMENTS

| | | | | |
|---|---|---|---|---|
| CN | 1121894 | A * | 5/1996 | A47G 25/904 |
| CN | 113499212 | A * | 10/2021 | A61B 42/50 |
| WO | WO0112032 | | 2/2001 | |
| WO | WO-2015138201 | A1 * | 9/2015 | A61B 42/50 |
| WO | WO-2022202867 | A1 * | 9/2022 | A47G 25/904 |

\* cited by examiner

*Primary Examiner* — Rakesh Kumar (57) ABSTRACT

A sterilized glove dispenser assembly includes a package which includes a panel and a pair of hand holes each extending into an interior of the package. A pair of gloves is contained within the package to insertably receive a respective one of the user's hands when the user pushes their hands through the hand holes for donning the gloves in a touch-less manner. A box is included which has a pair of hand holes each extending through the box and a pair of guides is each integrated into the box. Each of the guides slidably engages the panel of the package when the package is positioned in the box such that each of the hand holes in the panel of the package is aligned with a respective one of the hand holes in the box.

6 Claims, 6 Drawing Sheets

STERILIZED GLOVE DISPENSER ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to glove dispenser devices and more particularly pertains to a new glove dispenser device for donning gloves in a touch-less manner. The device includes a package that has a panel with hand holes and which contains a pair of gloves each aligned with a respective hand hole. The device includes a box with a pair of hand holes and the package is positioned in the box such that the hand holes in the panel are aligned with a respective one of the hand holes in the box. In this way a user can pass their hands through the hand holes in the box and the hand holes in the panel to don the gloves in a touch-less manner.

(2) Description of Related Art Including Information Disclosed Under 37 CFR 1.97 and 1.98

The prior art relates to glove dispenser devices including a glove donning device which includes a pair of donning cylinders which are negatively pressurized to inflate gloves in the donning cylinders for donning. The prior art discloses a mechanized glove dispenser which for automatically placing gloves on a user's hands for donning the gloves in a touch-less manner. The prior art discloses a glove formation device that includes a housing, an elastomeric sheet that is vacuum sealed around a user's hand and a laser cutting for trimming the elastomeric sheet. The prior art discloses a glove dispenser that includes a donning chute which retains a glove in an upside down orientation for donning the glove. The prior art discloses an electronic glove dispenser that dispenses a pair of gloves for a user to wear.

BRIEF SUMMARY OF THE INVENTION

An embodiment of the disclosure meets the needs presented above by generally comprising a package which includes a panel and a pair of hand holes each extending into an interior of the package. A pair of gloves is contained within the package to insertably receive a respective one of the user's hands when the user pushes their hands through the hand holes for donning the gloves in a touch-less manner. A box is included which has a pair of hand holes each extending through the box and a pair of guides is each integrated into the box. Each of the guides slidably engages the panel of the package when the package is positioned in the box such that each of the hand holes in the panel of the package is aligned with a respective one of the hand holes in the box.

A further embodiment of the disclosure comprises a method of donning gloves in a touch-less manner. The method includes the steps of providing a package which includes a panel and a bag attached to the panel. The panel has a pair of hand holes each extending into an interior of the package and the package is comprised of a sterile material. The steps include providing a pair of membranes that is each attached to the panel having each of the membranes covering a respective one of the hand holes. The steps include providing a pair of gloves that is each comprised of a sterile material and each of the gloves has a cuff. The steps include positioning each of the gloves in the package such that the cuff of each of the gloves is aligned with a respective one of the hand holes. The steps include providing a box that has a pair of guides and a pair of hand holes. Continuing, the steps include positioning the package in the box such that the panel slidably engages each of the guides thereby facilitating each of the hand holes in the panel to be aligned with a respective one of the hand holes in the box. The steps include inserting a user's hands through the hand holes in the box such that the user's hands are pushed through each of the membranes and into a respective one of the pair of gloves. Finally, the steps include removing the user's hands from the hand holes in the box having each of the gloves being worn on a respective one of the user's hands.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
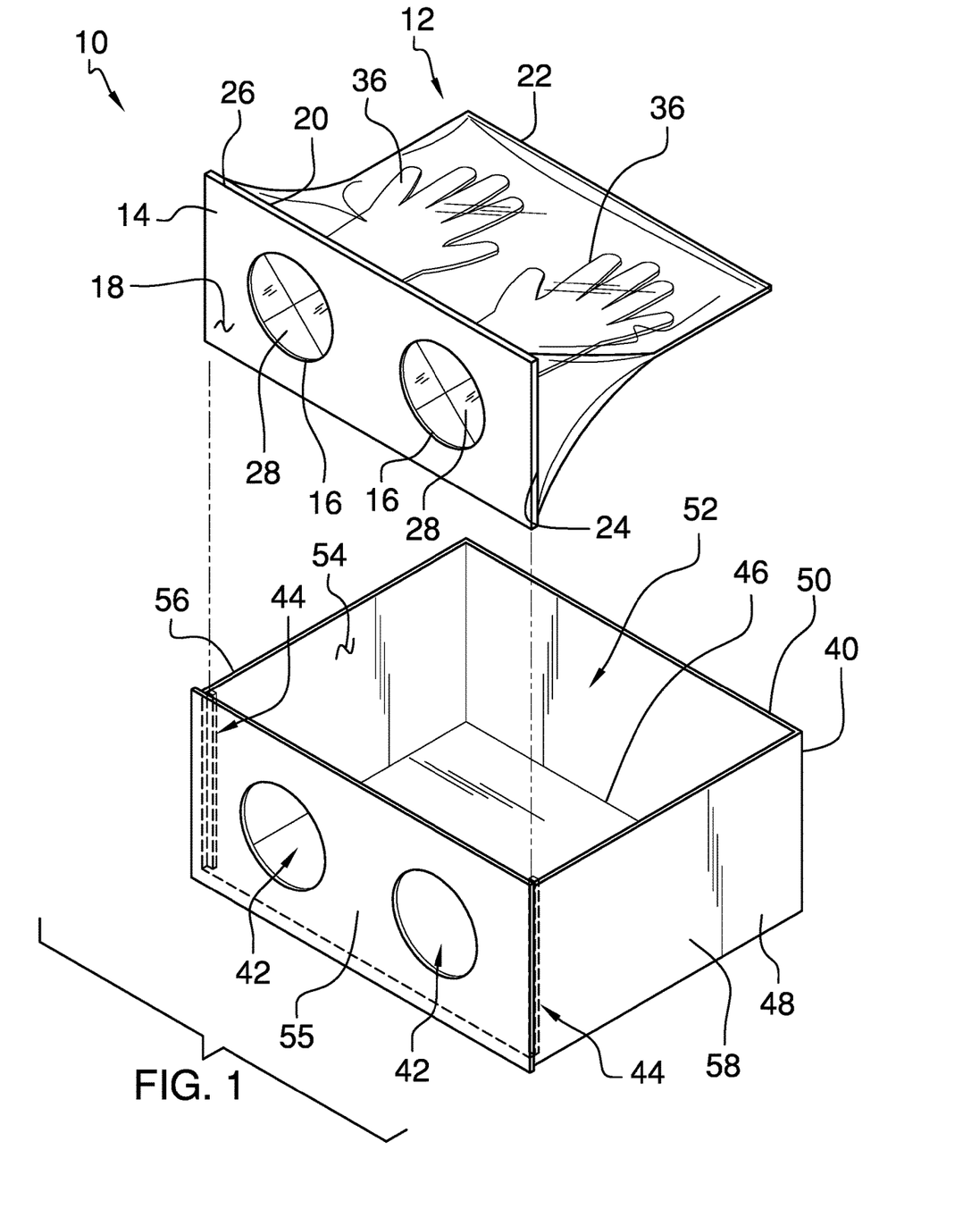
FIG. 1 is an exploded perspective view of a sterilized glove dispenser assembly according to an embodiment of the disclosure.
Figure 2:
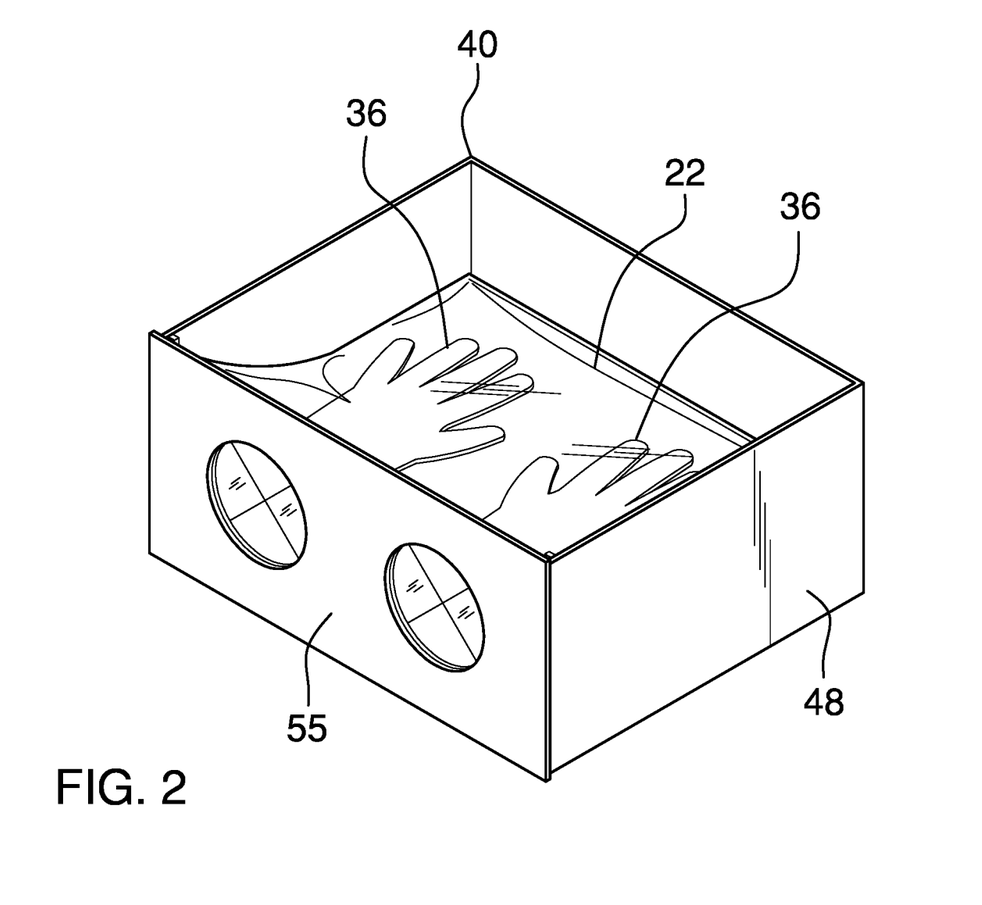
FIG. 2 is a front perspective view of an embodiment of the disclosure.
Figure 3:
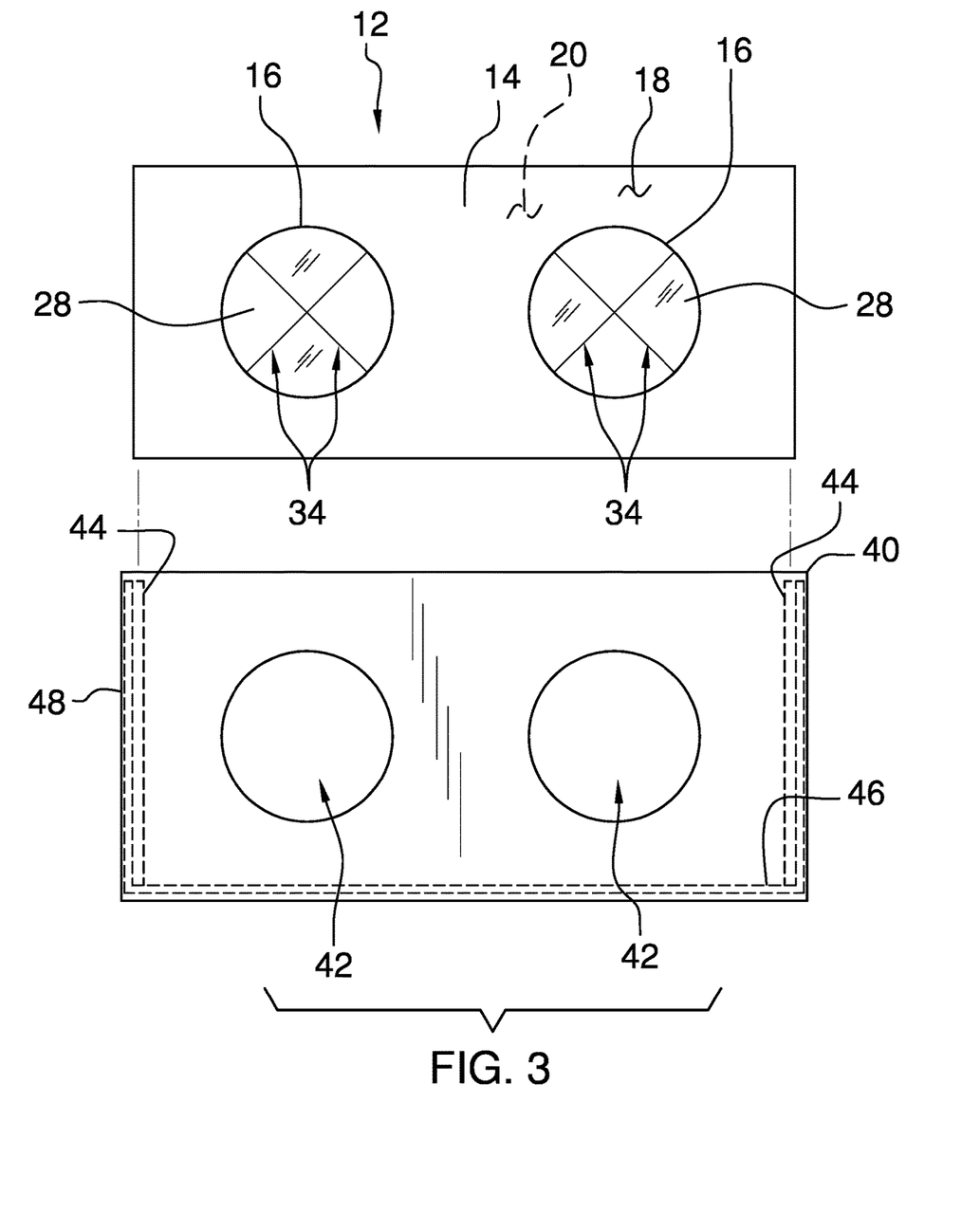
FIG. 3 is a front exploded view of an embodiment of the disclosure.
Figure 4:
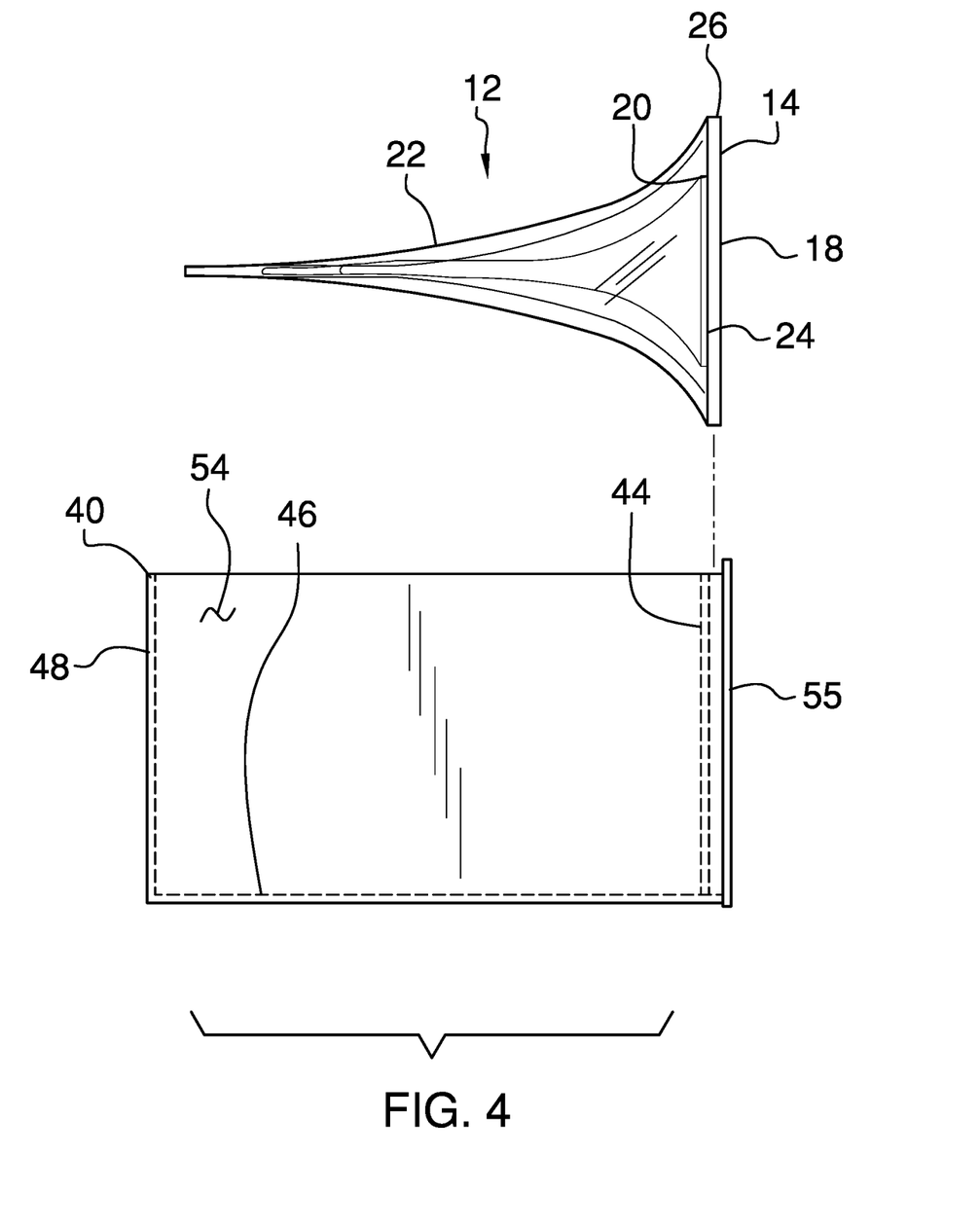
FIG. 4 is a right side exploded view of an embodiment of the disclosure.
Figure 5:
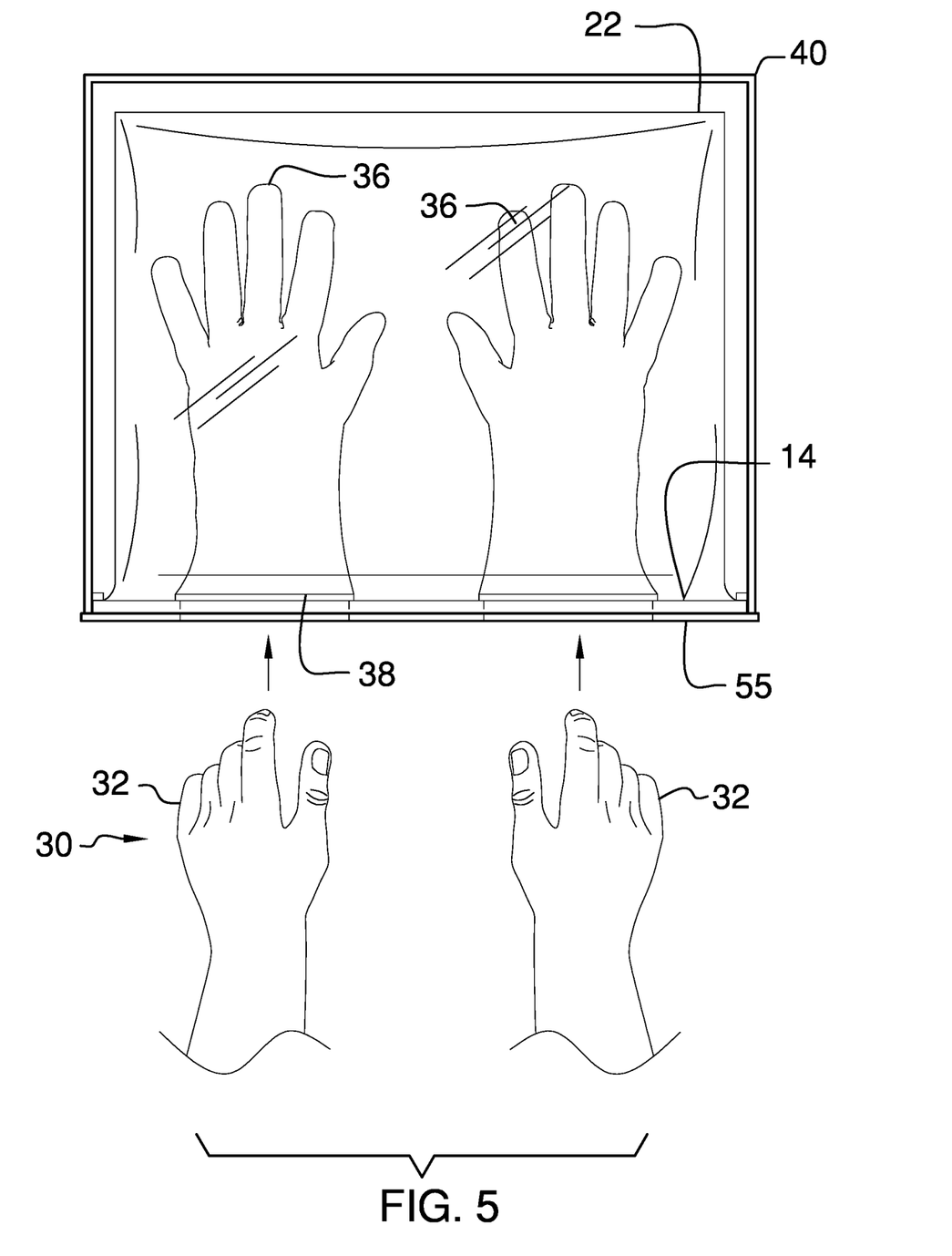
FIG. 5 is a top in-use view of an embodiment of the disclosure showing a user inserting their hands into hand holes in box.
Figure 6:
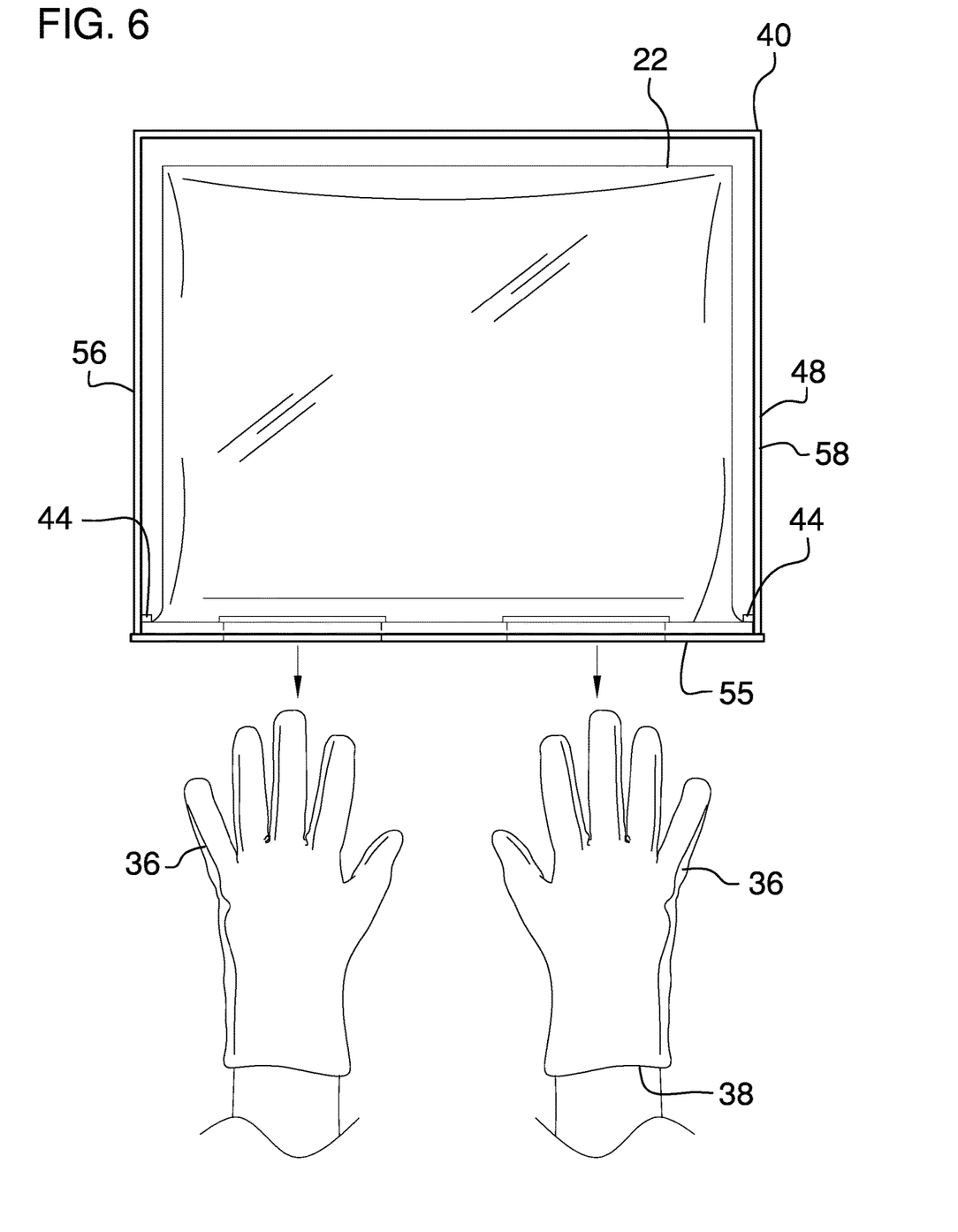
FIG. 6 is a top in-use view of an embodiment of the disclosure showing a user having donned a pair of gloves.

With reference now to the drawings, and in particular to FIGS. 1 through 6 thereof, a new glove dispenser device embodying the principles and concepts of an embodiment of the disclosure and generally designated by the reference numeral 10 will be described.

As best illustrated in FIGS. 1 through 6, the sterilized glove dispenser assembly generally comprises a package 12 that includes a panel 14. The panel 14 has a pair of hand holes 16 each extending into an interior of the package 12. The panel 14 has a front surface 18 and a back surface 20, and each of the hand holes 16 extends through the front surface 18 and the back surface 20. The package 12 includes a bag 22 that has a front edge 24 and the front edge 24 is bonded to the back surface 20 of the panel 14 such that the front edge 24 is oriented to extend along an entire perimeter edge 26 of the panel 14. The package 12 is comprised of a sterilized material thereby facilitating the package 12 to define a sterile environment.

A pair of membranes 28 each covers a respective one of the hand holes 16 in the panel 14 of the package 12. Each of the membranes 28 is comprised of a puncturable material to facilitate a user 30 to push each of their hands 32 through a respective one of the membranes 28. Additionally, each of the membranes 28 is comprised of a fluid impermeable material thereby preserving sterility of the sterile environment defined by the package 12. The membranes 28 may have tear lines 34 integrated into the membranes 28 to facilitate the membranes 28 to tear along the tear lines 34 when the user 30 pushes their hands 32 through the membranes 28.

A pair of gloves 36 is provided and each of the gloves 36 is contained within the package 12. Each of the gloves 36 is aligned with a respective one of the hand holes 16 thereby facilitating each of the gloves 36 to insertably receive a respective one of the user's hands 32 when the user 30 pushes their hands 32 through the membranes 28. In this way the pair of gloves 36 facilitates the user 30 to don the gloves 36 in a touch-less manner. Each of the gloves 36 is comprised of a sterilized material and each of the gloves 36 is comprised of a fluid impermeable material. In this way the pair of gloves 36 inhibits physical transmission of viruses and bacteria to or from the user's hands 32. Each of the gloves 36 may be comprised of a non-latex material that might commonly be employed on a surgical environment or other type of sterile environment. Each of the gloves 36 has a cuff 38 and the cuff 38 of each of the gloves 36 is aligned with the respective hand hole 16 has the cuff 38 abutting the back surface 20 of the panel 14.

A box 40 is provided that has a pair of hand holes 42 each extending through the box 40 and the box 40 has a pair of guides 44 that is each integrated into the box 40. Each of the guides 44 slidably engages the panel 14 of the package 12 when the package 12 is positioned in the box 40 such that each of the hand holes 16 in the panel 14 of the package 12 is aligned with a respective one of the hand holes 42 in the box 40. The box has a bottom wall 46 and a perimeter wall 48 extending upwardly from the bottom wall 46 and the perimeter wall 48 has a distal edge 50 defining an opening 52 into the box 40. The perimeter wall 48 has an interior surface 54 and the perimeter wall 48 has a front side 55, a first lateral side 56 and a second lateral side 58.

Each of the hand holes 42 associated with the box 40 extends through the front side 55 of the perimeter wall 48. Additionally, each of the guides 44 is positioned on a respective one of the first lateral side 56 and the second lateral side 58 of the perimeter wall 48. Each of the guides 44 extends between the distal edge 50 of the perimeter wall 48 and the bottom wall 46. Furthermore, each of the guides 44 is spaced an equal distance from the front side 55 of the perimeter wall 48. The panel 14 is positioned between each of the guides 44 and the front side 55 of the perimeter wall 48 when the package 12 is positioned in the box 40.

In use, the package 12, the gloves 36 and the box 40 are manufactured and sold as a single unit that is positioned in a location, such as a surgical operating room, where a user 30 would commonly need to don sterile gloves 36 in a sterilized environment. The user 30 would push each of their hands 32 through a respective membrane 28 to facilitate each of their hands 32 to extend into a respective glove 36. The user 30 subsequently removes their hands 32 from the box 40 with each of the gloves 36 being worn on the user's hands 32. In this way the user 30 can don the sterile gloves 36 in a touch-less manner to ensure the maximum level of protection against bacterial contamination between the gloves 36 and the sterilized environment. The gloves 36 are discarded after use and a new package 12, gloves 36 and box 40 are positioned for subsequent use.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A sterilized glove dispenser assembly for facilitating a user to don a pair of sterile gloves in a touch-less manner, said assembly comprising:

a package including a panel, said panel having a pair of hand holes each extending into an interior of said package;

a pair of membranes, each of said membranes covering a respective one of said hand holes in said panel of said package, each of said membranes being comprised of a puncturable material wherein each of said membranes is configured to facilitate a user to push each of their hands through a respective one of said membranes;

a pair of gloves, each of said gloves being contained within said package, each of said gloves being aligned with a respective one of said hand holes thereby facilitating each of said gloves to insertably receive a respective one of the user's hands when the user pushes their hands through said membranes wherein said pair of gloves is configured to facilitate the user to don said gloves in a touch-less manner;

a box having a pair of hand holes each extending through said box, said box having a pair of guides each being integrated into said box, each of said guides slidably engaging said panel of said package when said package is positioned in said box such that each of said hand holes in said panel of said package is aligned with a respective one of said hand holes in said box; and wherein said panel has a front surface and a back surface, each of said hand holes extending through said front surface and said back surface, said package including a bag having a front edge, said front edge being bonded to said back surface of said panel such that said front edge is oriented to extend along an entire perimeter edge of said panel, said package being comprised of a sterilized material thereby facilitating said package to define a sterile environment.

2. The assembly according to claim 1, wherein:

each of said gloves is comprised of a sterilized material;

each of said gloves being comprised of a fluid impermeable material wherein said pair of gloves is configured to inhibit physical transmission of viruses and bacteria to or from the user's hands; and each of said gloves has a cuff, said cuff of each of said gloves being aligned with said respective hand hole having said cuff abutting said back surface of said panel.

3. The assembly according to claim 1, wherein:

said box has a bottom wall and a perimeter wall extending upwardly from said bottom wall, said perimeter wall having a distal edge defining an opening into said box, said perimeter wall having an interior surface, said perimeter wall having a front side, a first lateral side and a second lateral side;

each of said hand holes associated with said box extends through said front side of said perimeter wall; and each of said guides is positioned on a respective one of said first lateral side and said second lateral side of said perimeter wall, each of said guides extending between said distal edge of said perimeter wall and said bottom wall, each of said guides being spaced an equal distance from said front side of said perimeter wall.

4. The assembly according to claim 3, wherein said panel is positioned between each of said guides and said front side of said perimeter wall when said package is positioned in said box.

5. A sterilized glove dispenser assembly for facilitating a user to don a pair of sterile gloves in a touch-less manner, said assembly comprising:

a package including a panel, said panel having a pair of hand holes each extending into an interior of said package, said panel having a front surface and a back surface, each of said hand holes extending through said front surface and said back surface, said package including a bag having a front edge, said front edge being bonded to said back surface of said panel such that said front edge is oriented to extend along an entire perimeter edge of said panel, said package being comprised of a sterilized material thereby facilitating said package to define a sterile environment;

a pair of membranes, each of said membranes covering a respective one of said hand holes in said panel of said package, each of said membranes being comprised of a puncturable material wherein each of said membranes is configured to facilitate a user to push each of their hands through a respective one of said membranes, each of said membranes being comprised of a fluid impermeable material thereby preserving sterility of said sterile environment defined by said package;

a pair of gloves, each of said gloves being contained within said package, each of said gloves being aligned with a respective one of said hand holes thereby facilitating each of said gloves to insertably receive a respective one of the user's hands when the user pushes their hands through said membranes wherein said pair of gloves is configured to facilitate the user to don said gloves in a touch-less manner, each of said gloves being comprised of a sterilized material, each of said gloves being comprised of a fluid impermeable material wherein said pair of gloves is configured to inhibit physical transmission of viruses and bacteria to or from the user's hands, each of said gloves having a cuff, said cuff of each of said gloves being aligned with said respective hand hole having said cuff abutting said back surface of said panel; and a box having a pair of hand holes each extending through said box, said box having a pair of guides each being integrated into said box, each of said guides slidably engaging said panel of said package when said package is positioned in said box such that each of said hand holes in said panel of said package is aligned with a respective one of said hand holes in said box, said box having a bottom wall and a perimeter wall extending upwardly from said bottom wall, said perimeter wall having a distal edge defining an opening into said box, said perimeter wall having an interior surface, said perimeter wall having a front side, a first lateral side and a second lateral side, each of said hand holes associated with said box extending through said front side of said perimeter wall, each of said guides being positioned on a respective one of said first lateral side and said second lateral side of said perimeter wall, each of said guides extending between said distal edge of said perimeter wall and said bottom wall, each of said guides being spaced an equal distance from said front side of said perimeter wall, said panel being positioned between each of said guides and said front side of said perimeter wall when said package is positioned in said box.

6. A method of donning sterile gloves in a touch-less manner, the steps of the method comprising:

providing a package comprising a panel and a bag attached to said panel, said panel having a pair of hand holes each extending into an interior of said package, said package being comprised of a sterile material;

providing a pair of membranes, each of said membranes being attached to said panel having each of said membranes covering a respective one of said hand holes;

providing a pair of gloves each being comprised of a sterile material, each of said gloves having a cuff;

positioning each of said gloves in said package such that said cuff of each of said gloves is aligned with a respective one of said hand holes;

providing a box having a pair of guides and a pair of hand holes;

positioning said package in said box such that said panel slidably engages each of said guides thereby facilitating each of said hand holes in said panel to be aligned with a respective one of said hand holes in said box;

inserting a user's hands through said hand holes in said box such that the user's hands are pushed through each of said membranes and into a respective one of said pair of gloves; and removing the user's hands from said hand holes in said box having each of said gloves being worn on a respective one of the user's hands.

\* \* \* \* \*